United States Patent [19]

Wapner

[11] Patent Number: 4,548,200
[45] Date of Patent: Oct. 22, 1985

[54] ENDOTRACHEAL TUBE HOLDER

[75] Inventor: Herbert H. Wapner, Belmont, N.H.

[73] Assignee: Baka Manufacturing Company, Inc., Plainville, Mass.

[21] Appl. No.: 485,843

[22] Filed: Apr. 18, 1983

[51] Int. Cl.⁴ ........................................... A61M 25/02
[52] U.S. Cl. ........................ 128/207.17; 128/DIG. 26; 604/179; 604/180
[58] Field of Search ...................... 128/207.14, 207.17, 128/207.18, DIG. 15, DIG. 26; 604/174, 179, 604/180

[56] References Cited

U.S. PATENT DOCUMENTS

| 3,146,778 | 9/1964 | Krawiec | 128/DIG. 26 |
|---|---|---|---|
| 3,288,136 | 11/1966 | Lund | 604/180 |
| 3,878,849 | 4/1975 | Muller et al. | 604/179 |
| 3,924,636 | 12/1975 | Addison | 128/207.14 |
| 4,088,136 | 5/1978 | Hasslinger | 604/179 |
| 4,142,527 | 3/1979 | Garcia | 604/180 |
| 4,215,687 | 8/1980 | Shaw | 128/DIG. 15 |
| 4,313,437 | 2/1982 | Martin | 128/DIG. 15 |
| 4,326,515 | 4/1982 | Shaffer et al. | 128/DIG. 26 |
| 4,437,463 | 3/1984 | Ackerman | 128/207.17 |
| 4,445,894 | 5/1984 | Kovacs | 128/DIG. 26 |

Primary Examiner—Henry J. Recla
Assistant Examiner—Karin M. Reichle
Attorney, Agent, or Firm—Wolf, Greenfield & Sacks

[57] ABSTRACT

An endotracheal tube holder comprised of a strip of Velcro-type material carrying a dense array of hooks and a pressure sensitive adhesive on its back for attaching the strip to the endotracheal tube, and a band of soft material having loops for engaging the hooks to hold the tube by the strip and which is adapted to encircle the head of the patient. The ends of the band also carry Velcro-type strips with hooks which are adapted to engage the band to releasably secure it in place on the head.

8 Claims, 9 Drawing Figures

ENDOTRACHEAL TUBE HOLDER

INTRODUCTION

This invention relates to medical appliances and more particularly comprises an endotracheal tube holder.

It is now customary to secure an endotracheal tube to the head of a patient by the use of adhesive tape. The principal object of this invention is to provide a tape free holder which fits all patients, is comfortable for the patient, does not exert excessive pressure on the patient's head, discourages self or accidental removal and does not accidentally open.

In accordance with the present invention, the endotracheal tube holder comprises a short strip of Velcro-type material which is adapted to encircle the endotracheal tube and be held on the tube by a pressure sensitive adhesive on the back of the strip. The tube holder also includes a band which is made of a soft looped fabric designed to be engaged by and releasably hold Velcro-type material. The band is designed to encircle the Velcro strip on the tube so as to firmly engage it as well as to encircle the head of the patient to secure the tube in place. The ends of the band also carry Velcro-type closures which enable the ends of the band to be crossed behind the head and be attached to the body of the band to hold it in place.

The invention will be better understood and appreciated from the following detailed description of one embodiment thereof, selected for purposes of illustration and shown in the accompanying drawing.

BRIEF FIGURE DESCRIPTION

DETAILED DESCRIPTION

Figure 1:
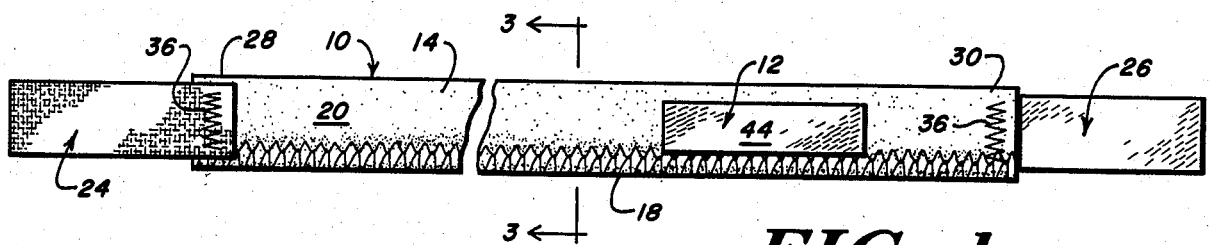
FIG. 1 is a plan view of an endotracheal tube holder constructed in accordance with this invention.
Figure 2:
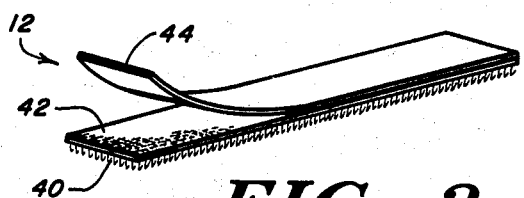
FIG. 2 is a perspective view of the tube strip showing the covering for the adhesive partially peeled from it.
Figure 3:
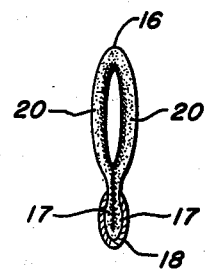
FIG. 3 is a cross sectional view of the holder taken along section line 3—3 of FIG. 1.

The endotracheal tube holder shown in FIGS. 1 to 4 includes a band 10 adapted to encircle the head and a strip 12 adapted to encircle the endotracheal tube. In use, the strip 12 on the tube is engaged by the band 10 which in turn encircles the head so as to support the tube in place.

The band 10 has a main body portion 14 made of a soft flocked cotton or some similar material having a looped surface adapted to serve as the female portion of a Velcro-type fastener. The body 14 may be approximately 27 inches long and is formed by folding it lengthwise upon itself (note fold 16 in FIG. 3) and its long edges 17 are stitched together as shown at 18. The band has a width greater than that of strip 12 to enable it to entirely cover the surface thereof. The body 14 formed in that fashion has the looped surface 20 on the outside exposed on both sides of the body so that either side may be engaged by the hook-like members of a Velcro-type material. The body 14 is very soft and is free of rough and abrasive edges which could irritate the skin when the band 10 is wrapped about the patient's head.

Figure 4:
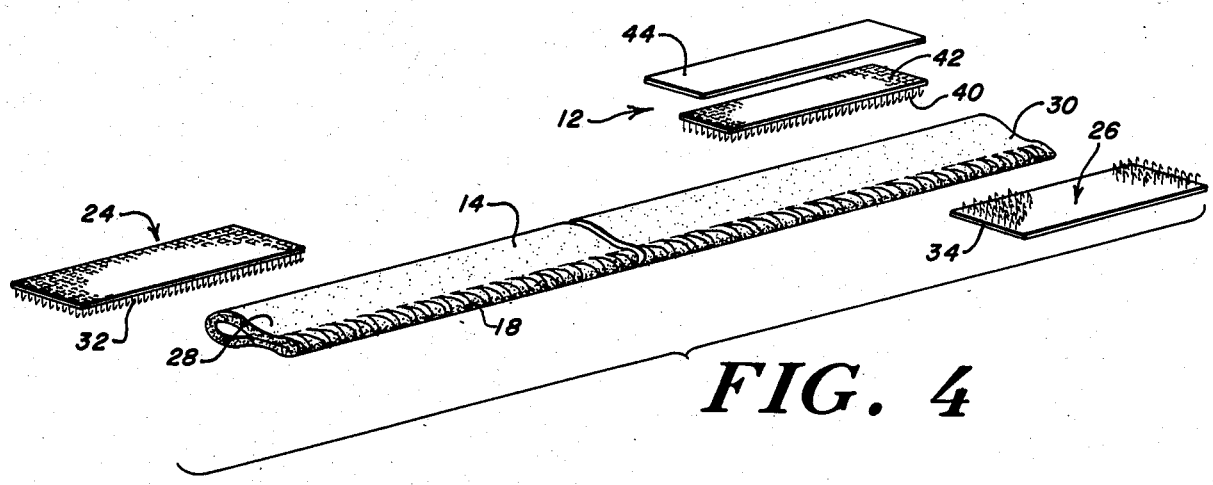
FIG. 4 is an exploded view of the tube holder showing the several parts before they are assembled.

Male Velcro-type strips 24 and 26 are sewn to the ends 28 and 30, respectively, of the body 14 with their hook-bearing faces 32 and 34 facing in opposite directions. The strips are shown in FIG. 1 to be secured in place on the opposite sides of the ends 28 and 30 by rows of stiching 36. Typically, the strips 24 and 26 are two inches in length and overlap the ends 28 and 30 of the body 14 by approximately one quarter inch. Thus, as viewed in FIGS. 1 and 4, the strip 24 is sewn to the upper surface of body 14 and its hook surface 32 faces downwardly. The strip 26 on the other hand is shown in FIGS. 1 and 4 to be sewn to the lower surface of body 14, and the hook-bearing surface 34 faces upwardly.

The strip 12 typically may be approximately one and one half inches in length and carries its hook-like fasteners 40 on one surface and carries a pressure-sensitive adhesive 42 on the other. The pressure-sensitive adhesive layer 42 in turn is covered by a removable paper covering 44 that may be easily peeled away to expose the adhesive when it is desired to mount the strip 12 on the endotracheal tube. Strip 12 may typically be between one quarter and three eights inch in width.

For packaging and storage, strip 12 may conveniently be attached to body 14 by means of the hook bearing surface 40 as suggested in FIG. 1. When stored in that fashion, the plastic covering 44 remains in place so as to prevent adhesive from sticking to any material in which it comes in contact. This arrangement is particularly suitable for packaging tube holders either individually or in bulk.

Figure 5:
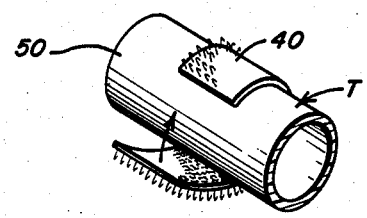
FIG. 5 is a fragmentary perspective view of an endotracheal tube showing the manner in which the strip of FIG. 2 is applied to it.
Figure 6:
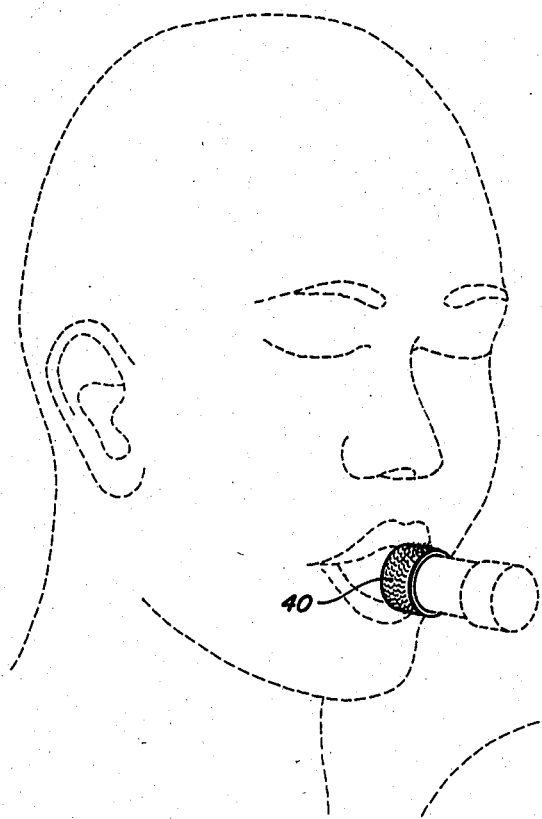
FIGS. 6-9 are pictorial views and show the manner in which the holder is used to retain the tube in place on the patient.
Figure 7:
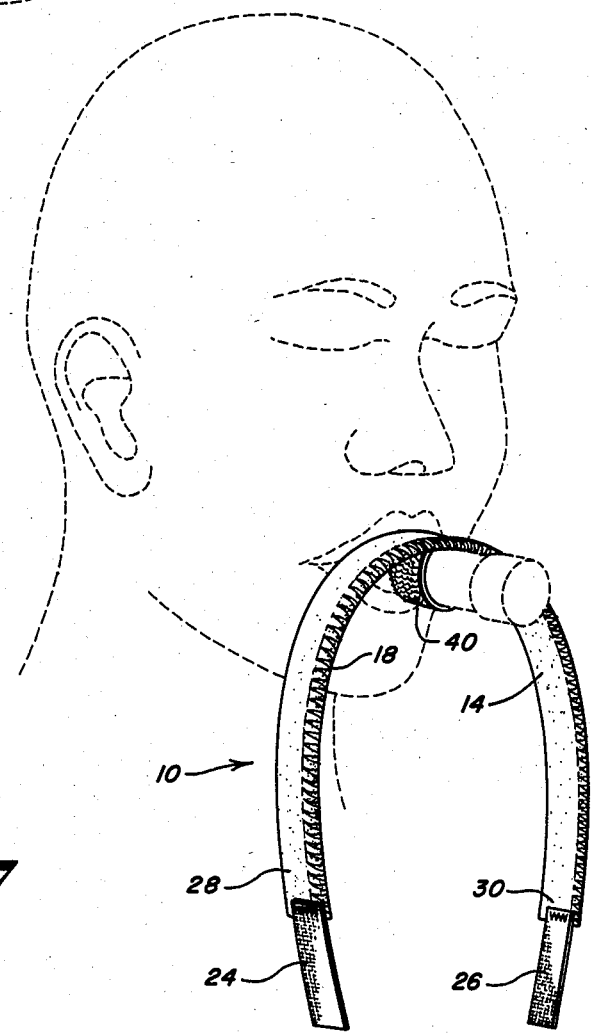

The manner in which the endotracheal tube holder is used is pictorially illustrated in FIGS. 5 to 9. To mount the strip 12 on the endotracheal tube, the strip is first cut so as to conform its length to the circumference of the endotracheal tube. Preferably the strip is cut either so as to equal the circumference of the tube or is slightly less than the circumference so that the ends of the strip do not overlap when the strip is adhered to the tube. In FIG. 5, strip 12 is shown cut to length (the strip may, or course, require no cutting if its length conforms to the circumference), and the backing 44 is peeled from the strip so as to expose the pressure sensitive adhesive layer 42. The adhesive layer is then applied to the surface of the endotracheal tube T just forward of the tube number designation 50 provided on the tube for record keeping purposes. After the endotracheal tube has been placed in the mouth of the patient as in FIG. 6, the strip 12 then is applied to the tube, with the hook-bearing surface 40 exposed. The band 10 is laid over the top of the tube with its sewn edge 18 facing away from the face of the patient as shown in FIG. 7. The band 10 is placed in that position so that its mid section overlies and is engaged by the hooks 40 of the strip 12 on the tube. The Velcro strips 24 and 26 hang downwardly from the ends 28 and 30 of the body 14.

Figure 8:
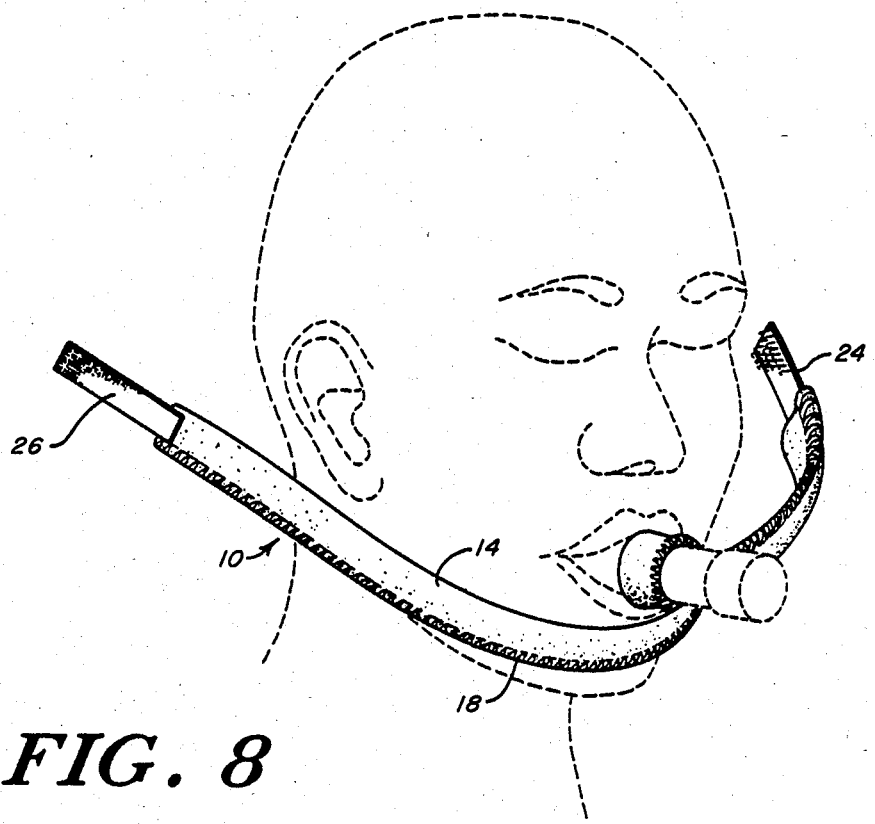

Next, the body 14 of the band 10 is crossed underneath the endotracheal tube T as shown in FIG. 8 so that the entire hooked surface 40 of the strip 12 is engaged by the body so as to maximize the grip of the band on the Velcro-type strip 12. This is done while maintaining the sewn edge 18 away from the face.

Figure 9:
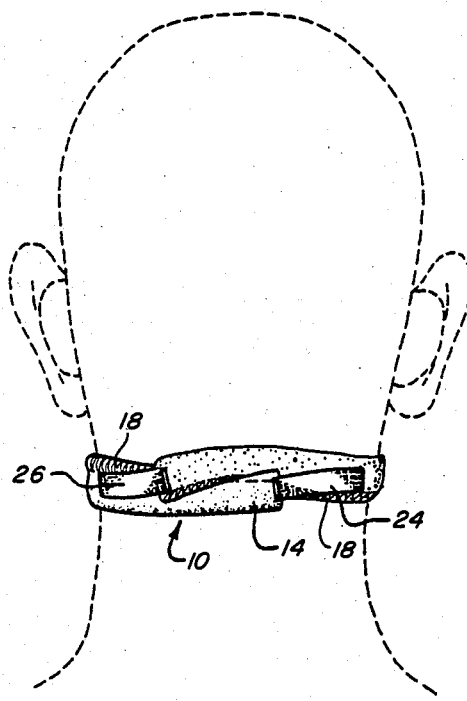

To complete the application of the tube holder, the ends of the band are pulled firmly about the head, and the band is criss-crossed behind the head and the hooked surfaces 32 and 34 of the strips 24 and 26 on the band ends are secured to the body 14 as shown in FIG. 9. Applied in that fashion, the band is firmly held in place about the head and the endotracheal tube in turn is held firmly in the mouth of the patient.

For maximum comfort, there should not be any upward or downward pull on the endotracheal tube T by the band 10. Should a downward pull exist after the application of the holder in the manner described above, the band may be reversed from the position shown in FIGS. 7 and 8 so that the band crosses the strip 12 above the tube T rather than below it. The sewn edge 18 of the body, however, should remain disposed away from the face. When the band is reversed, it will cover the upper lip of the patient rather than the chin when the band is pulled back to encircle the head. This arrangement may actually be preferred by some professionals.

From the foregoing description it will be appreciated that the tube holder of this invention may be applied very conveniently by a nurse, doctor or other attendant. There is no adhesive in contact with the skin of the patient which may cause discomfort either when in use or when being removed, and the holder may be opened and removed very quickly for any reason. Furthermore, the holder may be readily adjusted without creating any discomfort for the patient. The band made of a very soft material provides maximum patient comfort and eliminates totally the use of the all tape.

Those skilled in the art will appreciate that numerous modifications may be made of this invention without departing from its spirit. Therefore, it is not intended to limit the breadth of this invention to the single embodiment illustrated and described. Rather, it is intended that the scope of the invention be determined by the appended claims and their equivalents.

What is claimed is:

1. An endotracheal tube holder for securing an endotracheal tube when the latter is disposed in the mouth of a patient comprising a first strip of Velcro-type fastening material having a pressure sensitive adhesive on one side surface adapted to be adhered about the circumference of the endotracheal tube on the portion of the tube disposed outside the mouth of the patient, said strip having hook-like fasteners on its reverse side surface which are exposed when the strip is adhered to the tube, a band of soft looped fabric material having two free end portions and an elongated intermediate portion therebetween, said intermediate portion being adapted to be wound about the first strip on the tube such that the hook-like fasteners releasably engage the soft looped fabric, said end portions adapted to extend around the head of the patient and overlap each other and the band, and additional short strips of Velcro-type material attached to each end portion of the band, respectively, and having hook-like fasteners adapted to secure the end portions of the band to the intermediate portion of the band behind the head of the patient.

2. An endotracheal tube holder as defined in claim 1 further characterized by said band having both top and bottom side surfaces made of the soft looped fabric.

3. An endotracheal tube holder as defined in claim 2 further characterized by said band being of tubular configuration by folding the material of the band lengthwise and seaming the long edges of the band together.

4. An endotracheal tube holder as defined in claim 1 further characterized by the additional strips being secured at one end to the respective end portions of the band so as to extend beyond the looped fabric material of the band.

5. An endotracheal tube holder as defined in claim 1 further characterized by the first strip being adapted to be stored on the band with the hook-like fasteners facing and secured to the looped material of the band, and a removable cover adapted to cover the pressure sensitive adhesive when the first strip is stored on the band.

6. An endotracheal tube holder as defined in claim 1 further characterized by said band being separated and independent from the first strip and adapted to be wound about said strip so as to completely cover the hook-like fasteners on said first strip.

7. An endotracheal tube holder as defined in claim 1 further characterized by said band being wider than the first strip so that it entirely covers the hook-like fasteners on the first strip when the band is wound about said strip.

8. An endotracheal tube holder as defined in claim 1 further characterized by said additional strips having hook-like fasteners covering only one side surface thereof, said additional strips being secured at one end to the respective end portions of the band so as to extend beyond the looped fabric material and on opposite side surfaces of the band, respectively, with the hook-like fasteners adjacent said band such that the hook-like fasteners of the additional strips face in opposite directions.

* * * * *